United States Patent [19]

Winterton et al.

[11] Patent Number: 5,074,663

[45] Date of Patent: Dec. 24, 1991

[54] MULTIPLE INTERNAL REFLECTION CELL HAVING VENTED DUAL SEALS

[75] Inventors: Richard C. Winterton, Midland; Delmar R. Lafevor, Sanford, both of Mich.

[73] Assignee: The Dow Chemical Company, Midland, Mich.

[21] Appl. No.: 597,940

[22] Filed: Oct. 15, 1990

[51] Int. Cl.$^5$ .................... G01N 21/05; G01M 3/04
[52] U.S. Cl. ........................ 356/244; 73/40; 73/46; 340/605; 356/246; 356/440
[58] Field of Search ............... 356/300, 244, 246, 410, 356/440; 250/576; 340/603, 605; 73/40, 40.7, 46, 49.8

[56] References Cited

U.S. PATENT DOCUMENTS

| | | | |
|---|---|---|---|
| 3,641,542 | 2/1972 | Grove et al. | 340/605 |
| 4,197,531 | 4/1980 | Wentworth, Jr. | 340/605 |
| 4,988,155 | 1/1991 | Harner et al. | 356/440 X |

FOREIGN PATENT DOCUMENTS 3234198  9/1988  Japan ..................... 73/46

Primary Examiner—Vincent P. McGraw
Attorney, Agent, or Firm—Timothy S. Stevens

[57] ABSTRACT

An improvement upon cylindrical MIR element cells of the type that have a single seal at the openings of the cell body through which the cylindrical MIR element extends. The improvement is: (1) to position an additional seal between each such opening and the cylindrical MIR element so that there is a sealed space between the second seal and the original seal at each such opening; and (2) to position at least two passageways through the body of the cell, each such passageway in fluid communication with each of the above formed sealed spaces so that any leakage of a sample past the original seal is vented from the cell via one of the passageways. In a highly preferred embodiment of the present invention the portion of the cell body surrounding each such opening is made demountable and is provided with additional passageways and seals so that a purge fluid can be flowed through the passageways to a flow through detector to detect any leakage of a fluid sample past one of the original seals.

8 Claims, 2 Drawing Sheets

MULTIPLE INTERNAL REFLECTION CELL HAVING VENTED DUAL SEALS

FIELD OF THE INVENTION

The present invention is in the field of multiple internal reflection cells for spectroscopic analysis of fluid samples and more particularly the present invention relates to the sealing of a cylindrically shaped multiple internal reflection element of such a cell to the body of the cell.

BACKGROUND OF THE INVENTION

Multiple internal reflection (MIR) cells having a cylindrical MIR element (now called "circle cells" by some) appear to be initially disclosed in U.S. Pat. No. 3,017,802 issued on Jan. 23, 1962 to Walter Witt. U.S. Pat. No. 3,370,502, issued on Feb. 27, 1968 to Paul A. Wilks, Jr, described a cone-ended cylindrical MIR element. U.S. Pat. No. 4,595,833, issued on Jun. 17, 1986 to Donald W. Sting, disclosed ingenious optical elements for efficiently introducing infrared (IR) light into one end of a cone-ended cylindrical MIR element and for collecting IR light from the other end of such an element. The invention of Sting is commercially available from the Spectra-Tech division of Barnes Analytical, Stamford, Conn. as, for example, cell model 0005-001. Cylindrical MIR element cells are also commercially available from Wilks Scientific Corporation, South Norwalk, Conn. and from Axiom Analytical, Laguna Beach, Calif.

Cylindrical MIR element cells generally comprise a cell body. The cell body has a cavity within it. The cell body also has two apertures in it communicating with the cavity so that a cylindrical MIR element can be positioned in the cavity with the ends of the MIR element exposed to the exterior of the body at the apertures. An annular space remains in the cavity between the MIR element and the body. A fluid sample is flowed into this annular space. The MIR element is generally sealed to the body at each aperture in the body by the use of a single O-ring.

As discussed in the Witt patent, circle cells were developed for on-stream spectrometric analysis. As discussed in the Sting patent, cylindrical MIR element cells are uniquely applicable for on-stream spectrometric analysis. Despite the advancements made by Witt, Wilks, Sting and others over the years since 1962, however, a problem remained in on-stream analysis of industrial process streams using such cells. This problem was the possibility of leakage between the MIR element and one or both of the apertures in the cell body due to seal failure.

A leaking cell in an industrial on-line analyzer can be a serious problem, especially since such analyzers are usually not continuously attended. For example: (1) if the process stream is flammable, then there can be a fire or explosion hazard; or (2) if the process stream is toxic, then there can be a toxic release problem. It would be an advance in the art of on-stream chemical process analysis using cylindrical MIR element cells if a sealing means were developed that: (1) did not leak; or (perhaps more realistically) (2) that safely handled any leak that did occur.

SUMMARY OF THE INVENTION

The present invention is an advance in the art of cylindrical MIR element cells for on-stream spectrometric analysis because a means is disclosed to detect and/or safely handle such a seal leak.

The improvement of the present invention upon the above described cylindrical MIR element cell is: (1) to position an additional seal means between each aperture of the cell and the cylindrical MIR element extending through the aperture so that there is a sealed space between the second seal means and the original seal means at each such aperture; and (2) to position at least two passageways through the body of the cell, each such passageway in fluid communication with each of the above formed sealed spaces so that any leakage of a sample past the original seal is vented from the cell via one of the passageways.

In a highly preferred embodiment of the present invention the portion of the cell body surrounding each such aperture, herein termed a purge ring, is made demountable and is provided with additional passageways and seals so that a fluid can be flowed through the passageways to a flow through detector to detect any leakage of a fluid sample past one of the original seals.

DETAILED DESCRIPTION OF THE INVENTION

Figure 1:
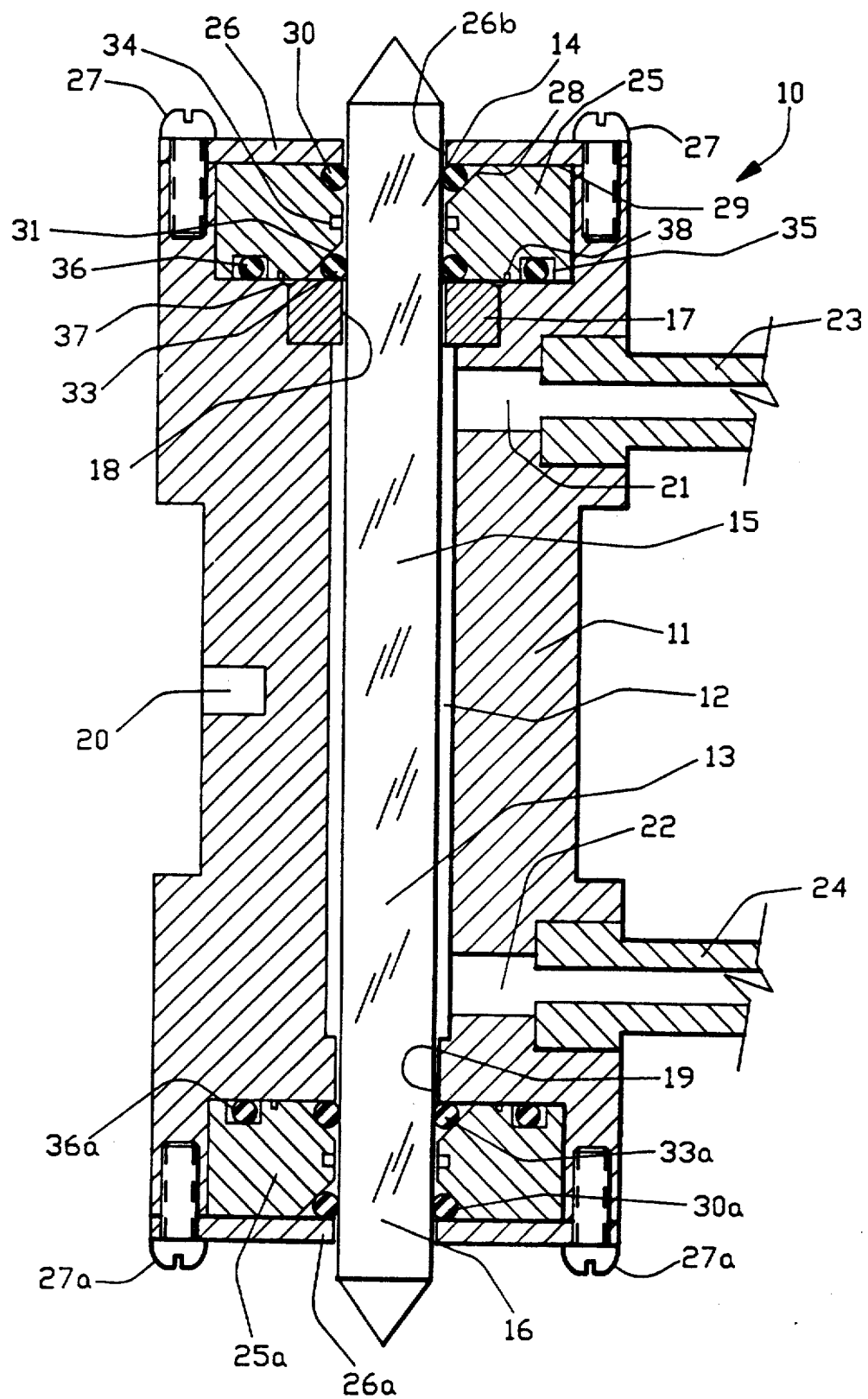
FIG. 1. is a cross sectional, side view of a highly preferred embodiment of the present invention showing a cone-ended cylindrical MIR element positioned in the cavity of the cell body and at each end thereof a purged ring retained to the cell body by a washer.

Referring now to FIG. 1, therein is shown a cross sectional, side view of a highly preferred cell 10 of the present invention. The cell 10 has a body 11 defining a cavity 12 therein. The cell 10 is made of the well known corrosion resistant metal alloy Hastelloy B-2. A cone-ended cylindrical MIR element 13, having a first end portion 14, a second end portion 16 and a central portion 15, is positioned within the body 11 with the central portion 15 of the cylindrical MIR element 13 positioned within the cavity 12 of the body 11. The body 11 has a ring-shaped insert portion 17 made of Hastelloy B-2 alloy. The mouth 18 of the insert portion 17 of the body 11 is the first aperture through the body 11 and this aperture is in communication with the chamber 12. The purpose of the insert portion 17 is to allow the machining of the cavity 12 in the body 11 with a drill rather than with a boring bar. Hastelloy B-2 is more easily machined with a drill than with a boring bar. The body 11 also has a second aperture 19 therethrough in communication with the chamber 12. The second end portion 16 of the cylindrical MIR element 13 is positioned through the second aperture 19. The first end portion 14 of the cylindrical MIR element 13 is positioned through the first aperture which is the mouth 18 of the insert portion 17. An index hole 20 is drilled into the body 11 and the body 11 is machined adjacent to the hole 20 so that this portion of the cell 10 has the same shape as the above discussed Spectra-Tech cell model 0005-001.

Thus, the cell 10 fits a standard Spectra-Tech cell saddle for the model 0005-001 cell.

A fluid sample passageway 21 is drilled into the body 11. A fluid sample passageway 22 is also drilled into the body 11. A nozzle 23 is electron beam welded to the body 11 coaxial with the passageway 21. A nozzle 24 is also electron beam welded to the body 11 coaxial with the passageway 22. Thus, a fluid sample can be flowed into and out of the chamber 12.

A demountable portion of the cell body 11 is a first purged ring 25 positioned adjacent to the first aperture with the first end portion 14 of the cylindrical MIR element 13 extending through the mouth of the ring 25 which is an extension of the first aperture. The ring 25 rests within a recess in the body 11 as shown and is retained in this recess by a first washer 26 which is removably fastened to the body 11 by screws 27. The first end portion 14 of the cylindrical MIR element 13 extends through the mouth 26b of the washer 26.

Figure 2:
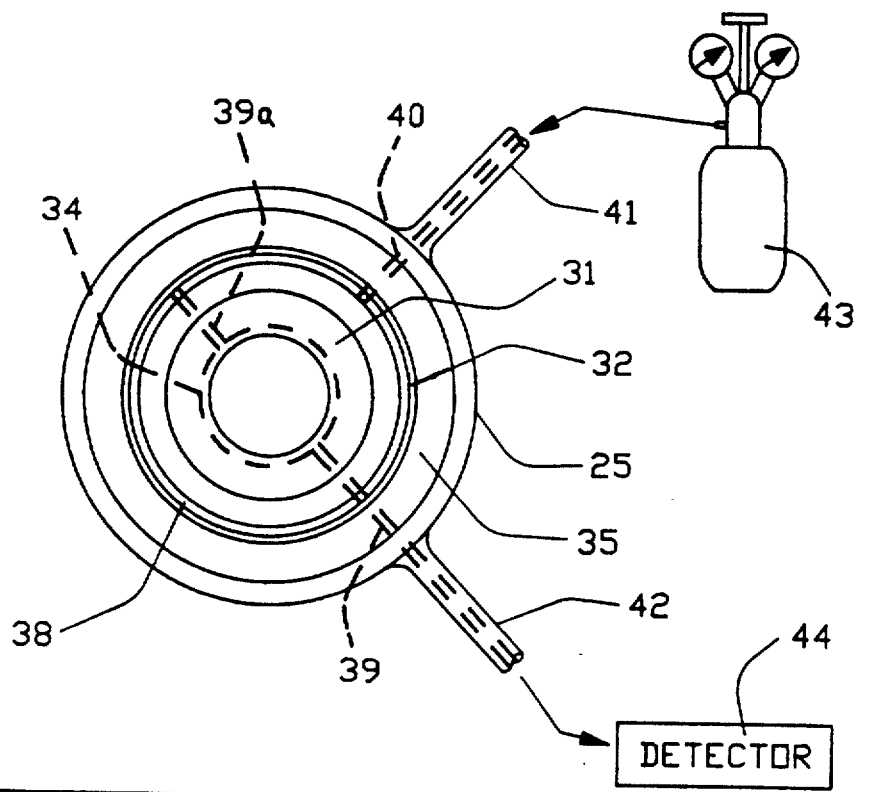
FIG. 2. is a full view of the interior side of one of the purged rings showing various passageways therethrough by dotted lines and showing a supply of compressed gas in fluid communication with one of these passageways and a flow-through detector in fluid communication with another of these passageways.
Figure 3:
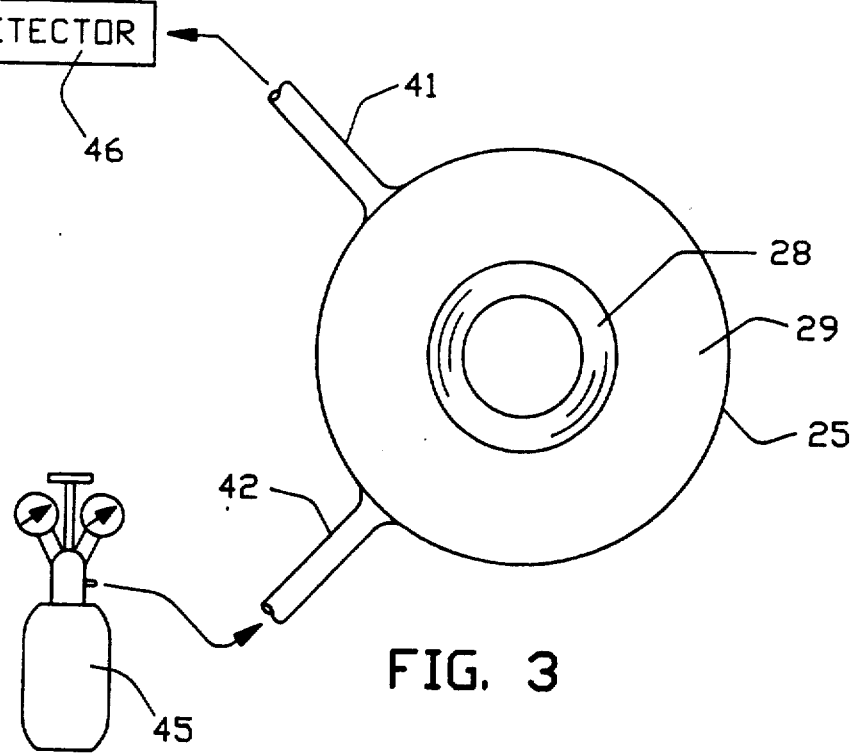
FIG. 3. is a full view of the exterior side of one of the purged rings showing the opposite arrangement of a supply of compressed gas and a flow-through detector.

The ring 25 is shown in greater detail and from different directions in FIGS. 2 and 3. The ring 25 has a tapered portion 28 on its exterior side 29. An O-ring 30, made of KALREZ brand Fluoroelastomer, is compressed between the tapered portion 28 of the ring 25, the first end 14 of the circular MIR element 13 and the washer 26. The O-ring 30 is the second seal of the cell 10 and it seals the ring 25 to the first end 14 of the circular MIR element 13. The ring 25 has another tapered portion 31 on its interior side 32. An O-ring 33 made of KALREZ brand Fluoroelastomer, is compressed between the tapered portion 31 of the ring 25, the first end 14 of the circular MIR element 13 and the insert portion 17. The O-ring 33 is the first seal of the cell 10 and it seals the ring 25 to the first end 14 of the circular MIR element 13. Thus, there is a first sealed space between the first seal and the second seal of the cell 10. A groove 34 is cut in the mouth of the ring 25 and the groove 34 is within the sealed space between the first and second seals. A gland 35 is cut in the face 32 of the ring 25. An O-ring 36, made of KALREZ brand fluoroelastomer, is compressed between the gland 35 of the ring 25 and the body 11. The O-ring 36 is the third seal of the cell 10. The insert portion 17 is sealed to the body 11 of the cell 10 by an electron beam weld 37. The electron beam weld 37 is preferably deep and penetrating and not the shallow weld shown in FIG. 1 as the weld 37. The weld 37 is the seventh seal of the cell 10. Thus, there is a second sealed space between the first seal and the third seal of the cell 10. A groove 38 is cut in the interior face 32 of the ring 25 and the groove 38 is within the second sealed space.

Referring now to FIG. 2, a first, straight passageway 39 is drilled into the ring 25 to the groove 34. A second, L-shaped passageway 40 is drilled into the ring 25 to the groove 38 A third, L-shaped passageway 39a is drilled into the ring 25 to connect the groove 38 and the groove 34. A tube 41 is brazed to the ring 25 so that the tube 41 is coaxial with the passageway 40. A tube 42 is likewise brazed to the ring 25 so that the tube 42 is coaxial with the passageway 39.

Referring again to FIG. 2, a cylinder of compressed nitrogen 43 is used to direct a flow of nitrogen purge gas into the tube 41. An electrical conductivity detector 44 is connected to the tube 42. When the ring 25 as shown in FIG. 2 is in its place in the cell 10 as shown in FIG. 1, then the flowing nitrogen passes sequently down the tube 41, down the passageway 40, into the groove 38 and the second sealed space, down the passageway 39a, into the groove 34 and the first sealed space, down the passageway 39, down the tube 42 and then through the detector 44. If there is a leak of an electrically conducting sample fluid in the cavity 12 past the O-ring 33, then this leaking sample fluid is carried by the flowing nitrogen to the detector 44 to be detected. This detection indicates that the cell should be overhauled. The O-ring 36 and the O-ring 30 thus serve as secondary safety seals and ordinarily are not exposed to the fluid sample.

Referring now to FIG. 3, an alternative system is shown wherein the flow pattern described above is reversed. A cylinder of compressed helium 45 is used to direct a flow of helium purge gas into the tube 42 and a thermal conductivity detector 46 is used to detect the leakage. It should be understood that the specific purge fluid of the present invention is not critical in the present invention and neither is its direction of flow through the purge ring. Further, the specific detector used to detect a leak is not critical in the present invention as long as it detects the leaking sample in the purge fluid. The purge fluid can be a gas and can be a liquid. Examples of suitable detectors in the present invention when the purge fluid is a gas are gas chromatography detectors such as thermal conductivity detectors, electron capture detectors, and ionization detectors. Examples of suitable detectors in the present invention when the purge fluid is a liquid are liquid chromatography detectors such as electrical conductivity detectors, dielectric constant detectors and spectrophotometric detectors. If the sample fluid is radioactive, then a radiation detector can be used.

Referring now to FIG. 1, the end of the cell 10 surrounding the second end portion 16 of the cylindrical MIR element 13 is identical to the above described end of the cell 10 which surrounds the first end portion 14 of the cylindrical MIR element 13, except that the insert portion 17 is not used. Thus: there is a second purged ring 25a; a second washer 26a; screws 27a; a fourth O-ring 33a; a fifth O-ring 30a; and a sixth O-ring 36a. The purge ring 25a can be purged and any leak past the O-ring 33a detected just as above discussed for the purge ring 25.

The material of construction of body 11, the insert portion 17, the purge ring 25 and the purge ring 25a is not critical in the present invention and can include plastics and metals. Preferably they are made of a corrosion resistant metal or metal alloy such as nickel, tantalum or stainless steel. The specific choice depends on the corrosiveness of the fluid sample. Hastelloy B-2 is a highly preferred material in some applications.

The specific seal means used for the first, second, third, fourth, fifth and sixth seals of the present invention is not critical and can include sealants, gaskets and lip seals. However, O-rings are preferred and fluorelastomer O-rings, such as VITON brand fluoroelastomer and especially KALREZ brand fluoroelastomer O-rings, are higly preferred.

The cell shown in FIG. 1 is a specific example of many that could have been described. It should be understood that variations upon the design of the cell shown in FIG. 1 can be made while staying within the scope of the present invention. For example; the purge rings of the present invention need have only one passageway each; and the purge rings can be made integral with the body of the cell.

What is claimed is:

1. A multiple internal reflection cell for spectroscopic analysis of fluid samples, comprising:

(a) a body, the body defining a cavity therein, the body defining a first aperture therethrough in communication with the cavity, the body at least also defining a second aperture therethrough in communication with the cavity;

(b) a cylindrically shaped multiple internal reflection element having a first end portion, a second end portion and a central portion, the central portion of the cylindrically shaped multiple internal reflection element positioned within the cavity leaving a sample space between the body and the central portion of the cylindrically shaped multiple internal reflection element for a fluid sample, the first end portion of the cylindrically shaped multiple internal reflection element positioned within the first aperture, the second end portion of the cylindrically shaped multiple internal reflection element positioned within the second aperture;

(c) a first purged ring positioned adjacent to the first aperture with the first end portion of the cylindrically shaped multiple internal reflection element extending through the mouth of the first purged ring;

(d) a first washer removably fastened to the body and positioned adjacent to the first purged ring with the first end portion of the cylindrically shaped multiple internal reflection element extending through the mouth of the first washer so that the first washer retains the first purged ring in its position;

(e) a first seal means for sealing the first purged ring to the first end portion of the cylindrically shaped multiple internal reflection element;

(f) a second seal means for sealing the first purged ring to the first end portion of the cylindrically shaped multiple internal reflection element, the second seal means positioned apart from the first seal means so that there is a first sealed space between the first seal means and the second seal means;

(g) a third seal means for sealing the first purged ring to the body, the third seal means positioned apart from the first seal means so that there is a second sealed space between the third seal means and the first seal means;

(h) a first passageway positioned through the first purged ring in communication with the first sealed space;

(i) a second passageway positioned through the first purged ring in communication with the second sealed space;

(j) a third passageway positioned through the first and the second sealed space;

(k) a second purged ring positioned adjacent to the second aperture with the second end portion of the cylindrically shaped multiple internal reflection element extending through the mouth of the second purged ring;

(l) a second washer removably fastened to the body and positioned adjacent to the second purged ring with the second end portion of the cylindrically shaped multiple internal reflection element extending through the mouth of the second washer so that the second washer retains the second purged ring in its position;

(m) a fourth seal means for sealing the second purged ring to the second end portion of the cylindrically shaped multiple internal reflection element;

(n) a fifth seal means for sealing the second purged ring to the second end portion of the cylindrically shaped multiple internal reflection element, the fifth seal means positioned apart from the fourth seal means so that there is a third sealed space between the fourth seal means and the fifth seal means;

(o) a sixth seal means for sealing the second purged ring to the body, the sixth seal means positioned apart from the fourth seal means so that there is a fourth sealed space between the sixth seal means and the fourth seal means;

(p) a fourth passageway positioned through the second purged ring in communication with the third sealed space;

(q) a fifth passageway positioned through the second purged ring in communication with the fourth sealed space;

(r) a sixth passageway positioned through the second purged ring in communication between the third sealed space and the fourth sealed space.

2. The cell of claim 1 wherein the body, the first purged ring and the second purged ring each comprise a corrosion resistant metal alloy.

3. The cell of claim 2 wherein the corrosion resistant metal alloy is selected from the group consisting of tantalum, nickel, stainless steel and Hastelloy B-2.

4. The cell of claim 3 wherein the cell further comprises an additional ring and a seventh seal, the additional ring positioned between the first purged ring and the body with the first end portion of the cylindrically shaped multiple internal reflection element extending through the mouth of the additional ring, the seventh seal being between the additional ring and the body adjacent the second sealed space.

5. The cell of claim 4 wherein the additional ring comprises the same material as the body; wherein the seventh seal is made by electron beam welding and wherein the first, second, third, fourth, fifth and sixth seal means each comprise an O-ring.

6. The cell of claim 5, wherein each O-ring comprises KALREZ brand fluoroelastomer.

7. The cell of claim 1 further comprising a means for supplying a fluid under pressure in fluid communication with the first passageway and a flow through detector in fluid communication with the second passageway so that any leakage of a fluid sample from the sample space into the first space or the second space can be carried to the flow through detector to be detected.

8. The cell of claim 1 further comprising a means for supplying a fluid under pressure in fluid communication with the second passageway and a flow through detector in fluid communication with the first passageway so that any leakage of a fluid sample from the sample space into the first space or the second space can be carried to the flow through detector to be detected.

* * * * *

UNITED STATES PATENT AND TRADEMARK OFFICE
CERTIFICATE OF CORRECTION

PATENT NO. : 5,074,663
DATED : December 24, 1991
INVENTOR(S) : Richard C. Winterton, et. al.

It is certified that error appears in the above-indentified patent and that said Letters Patent is hereby corrected as shown below:

On the Title page, item [56], under References Cited, should have the following U.S. Patent Documents included on the list:

-- 570,726, 11/1896, E. C. Butts
 1,779,076, 10/1930, J. L. Ray
 3,017,802, 01/1962, W. Witt, 88/14
 3,370,502, 02/1968; P. A. Wilks, Jr., 88/14
 4,595,833, 06/1986, D. W Sting, 250/353--

Column 5, line 51, "(j) a third passageway positioned through the first and the second sealed space;", should correctly read --a third passageway positioned through the first purged ring in communication between the first sealed space and the second sealed space;--.

Signed and Sealed this

Seventeenth Day of August, 1993

*Attest:*

BRUCE LEHMAN

*Attesting Officer*   *Commissioner of Patents and Trademarks*